United States Patent [19]

Huggins

[11] 4,272,051
[45] Jun. 9, 1981

[54] APPARATUS FOR METERING FLUIDS

[76] Inventor: James A. Huggins, 551 W. Park Ave., Libertyville, Ill. 60048

[21] Appl. No.: 917,943

[22] Filed: Jun. 22, 1978

[51] Int. Cl.³ ............................................. F16K 7/06
[52] U.S. Cl. ......................................... 251/6; 251/9
[58] Field of Search .............................. 251/4, 6–10; 24/115 L

[56] References Cited

U.S. PATENT DOCUMENTS

| 3,215,394 | 11/1965 | Sherman | 251/4 |
| 3,625,472 | 12/1971 | Rychlik | 251/6 |
| 3,685,787 | 8/1972 | Adelberg | 251/6 |
| 3,893,468 | 7/1975 | McPhee | 251/6 X |
| 4,034,773 | 7/1977 | Huggins | 251/9 X |

Primary Examiner—Martin P. Schwadron
Assistant Examiner—H. Jay Spiegel
Attorney, Agent, or Firm—Trexler, Wolters, Bushnell & Fosse, Ltd.

[57] ABSTRACT

A clamp for providing a stable fluid flow rate through a flexible tubing has a channel having a bottom wall including an anvil for supporting the tubing and an opening along its entire length for readily receiving and supporting the tubing against the bottom wall and the anvil. The channel also includes a pair of slots adapted for receiving and retaining a tube-constricting means. The constricting means comprises a rotatable cam having a groove of varying depth along its surface which coacts with the anvil to define a reduced-flow passageway in the tubing. As the cam is rotated from an opened position, corresponding to a maximum fluid flow rate through the tubing, to a closed position, the groove presents to the tubing a plurality of similar triangles progressively reduced in size to reduce the flow passageway in the tubing.

18 Claims, 18 Drawing Figures

APPARATUS FOR METERING FLUIDS

BACKGROUND OF THE INVENTION

The present invention is generally directed to adjustable clamps and methods for controlling the rate of fluid flow through flexible plastic tubing and more particularly to an adjustable clamp and method for controlling the rate of fluid flow through flexible tubing such as used for intravenous infusion of liquid nourishment and/or medication.

The intravenous infusion of medicinal fluids is quite common in current medical practice. For example, anesthetics are infused intravenously during operations, and intravenous feeding is commonly employed in the post operative period. In addition, there are many patients whose illness either restricts their ability to take food orally or to digest food properly so taken, and then such patients must be fed intravenously for the duration of their illness.

The apparatus commonly employed for intravenous infusions includes a stand for supporting a bottle of the appropriate fluid in an elevated position above the patient. The bottle of fluid is supported in an inverted position to induce gravity flow of the fluid. A sterile intravenous set comprising a flexible plastic tubing and a plastic spike at one end of the tubing conducts the fluid from the bottle to the patient by gravity feed. The spike end of the flexible tubing is inserted into the bottle stopper and the needle is inserted into the patient's vein using approved sterile techniques. All air is eliminated within the tubing before the patient is infused by allowing the fluid to completely fill the tubing. The flow rate of the fluid through the tubing is controlled by an adjustable clamp on the tubing. The clamp controls the fluid flow rate by controlling the cross-sectional area of the tubing. In order to measure the flow rate with these devices it is necessary to count visually the number of drops of fluid per minute by watching the drops in the drop chamber located below the spike.

In the past, a problem has been encountered in maintaining a constant fluid flow rate through the flexible plastic tubing (usually polyvinyl) because of its physical characteristics. After the desired fluid flow rate has been set with the adjustable clamp, as by restricting a portion of the cross-section of the tubing, the plastic wall of the tubing tends to cold flow or deform slowly resulting in a progressive change in the cross-sectional area through which the fluid is flowing thereby progressively changing the fluid flow rate through the tubing. This requires frequent adjustment of the clamp in order to make sure that the correct fluid flow rate is maintained. Tests have shown that the standard intravenous set loses an average of 45% of its initial flow rate in ten minutes if not readjusted.

The adjustable clamps and methods fully disclosed and claimed in U.S. Pat. No. 4,034,773 which issued on July 12, 1977 in the name of the inventor of the present invention has significantly reduced the flexible tubing cold flow problem referred to above. The present invention provides a still further improvement on the invention in the aforesaid patent.

Another problem with prior art adjustable clamps for use in intravenous feeding is that they cannot be applied to the flexible tubing without disturbing the sterility of the intravenous sets. Intravenous sets are commonly supplied to medical facilities by suppliers who provide their own control clamps as a part of the sets. Unfortunately, these clamps cold flow and prior art clamps which control cold flow cannot be attached to the tubing of the finished set. The reason for this is that the prior art clamps are not adapted to be applied directly to the flexible tubing without disturbing the set sterility. Hence, there is a need in the art for a clamp which may be applied to the flexible tubing of an intravenous set for controlling cold flow without disturbing the sterile condition of the intravenous set.

OBJECTS AND SUMMARY OF THE INVENTION

It is therefore a general object of the present invention to provide a new and improved clamp for accurately controlling the fluid flow rate through a flexible tubing. In general, this is accomplished by clamping the tubing in such a manner that the cross-sectional area of the fluid flow passageway within the tubing is prevented from changing, once having been set, by the application of constant constricting forces on the tubing at spaced apart regions adjacent each side of the passageway transversely of the tubing.

It is a further object of the present invention to provide such a clamp wherein the constricting forces on the tubing are sufficient to preclude inadvertent pulling of the tubing longitudinally of the clamp which would otherwise result in a change of the fluid flow rate through the tubing.

It is a still further object of the present invention to provide a clamp for metering fluids through the flexible tubing of a sterile intravenous set which may be applied to the tubing without disturbing the sterile condition of the intravenous set.

The present invention therefore provides a clamp for providing a stable fluid flow rate through a flexible tubing. The clamp comprises a surface for supporting the tubing, which surface includes a first part and a pair of second parts extending in respective opposite directions from the first part, and constricting means forming an opposing structure to the support surface for confining the tubing therebetween. The opposing structure includes a first surface portion adjacent the supporting surface first part, a pair of peripheral surface portion, and a pair of intermediate surface portions between the first surface portion and the peripheral surface portions. The peripheral surface portions coact with the supporting surface second parts for compressing diametrically opposed wall portions of the tubing sufficiently to shut off the tubing at peripheral spaced apart regions. The first surface portions coact with the support surface first part for defining a space for a reduced-flow passageway in the tubing and the intermediate surface portions coact with the support surface second parts for constricting the tubing therebetween. The constricting means includes an arm structure pivotal relative to the support surface for gradually increasing the constricting contact surface area of the intermediate surface portions with the tubing along a line parallel to the support surface second parts and for gradually reducing the transverse dimension of the first surface portion and the space for a reduced-flow passageway in the tubing as the constricting means is pivoted from an open position to a closed position.

The present invention also provides a clamp for providing a stable fluid flow rate through a flexible tubing which is adapted to be readily mounted onto the tubing. The clamp comprises a body having a channel dimensioned to receive the tubing, the channel having a pair of side walls and a bottom wall including an anvil for supporting the tubing, and constricting means providing an opposed structure to the anvil and coacting with the anvil for controllably compressing the tubing to establish a stable fluid flow rate through the tubing. The channel has an opening along its entire length for receiving the tubing therein against the bottom wall and means for receiving and retaining the constricting means in an operating position spaced from and adjacent to the anvil.

BRIEF DESCRIPTION OF THE DRAWINGS

The features of the present invention which are believed to be novel are set forth with particularity in the appended claims. The invention, together with further objects and advantages thereof, may best be understood by reference to the following description in conjunction with the accompanying drawings and in the several figures of which like reference numerals indicate identical elements and in which:

DESCRIPTION OF THE PREFERRED EMBODIMENTS

Figure 1:
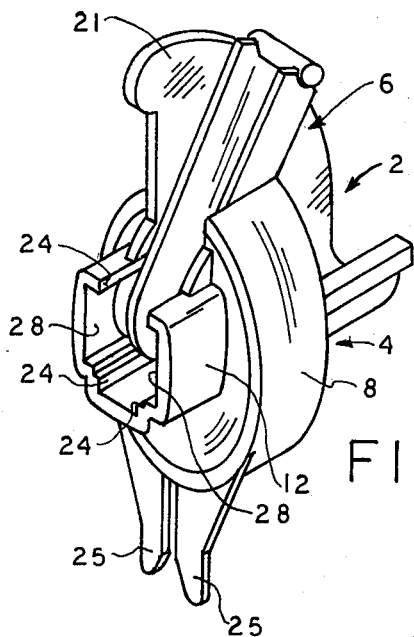
FIG. 1 is a perspective view of a clamp constructed in accordance with and embodying the present invention.
Figure 2:
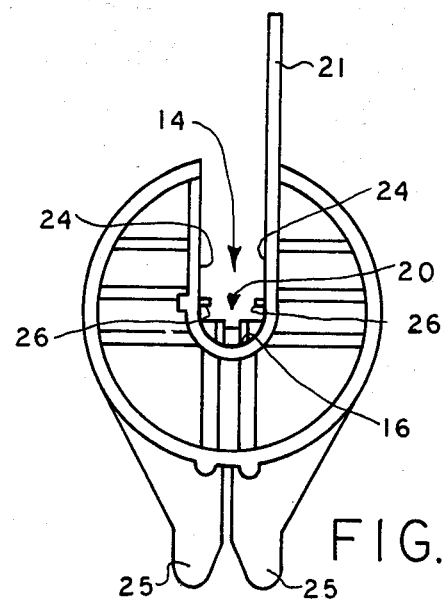
FIG. 2 is a view of the clamp of FIG. 1 looking towards the rearward end of the clamp with the cam and pivot arm removed.
Figure 3:
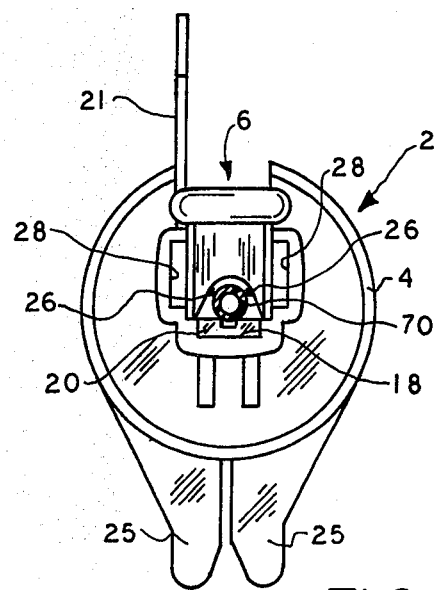
FIG. 3 is a view of the clamp of FIG. 1 looking towards the forward end of the clamp with the cam and pivot arm in place in juxtapositon to a flexible tubing and arranged prior to metering of fluid flow through the tubing.

Referring now initially to FIGS. 1 through 3 of the drawings, there is shown a clamp 2 which embodies the present invention. The clamp 2 generally comprises a body 4 and a cam and pivot arm 6. The body 4 includes a central, generally cylindrical, housing portion 8 having a rearward extension 10 and a forward extension 12. A channel 14 extends entirely through the housing and includes a bottom wall having an arcuate portion 16 extending from the central housing portion 8 through the rearward extension 10 and a relatively flat portion 8 extending from the central portion through the forward extension 12. Separating the arcuate bottom wall portion 16 and the substantially flat bottom wall portion 18 is an anvil structure 20 best seen in FIG. 4. The anvil structure 20 includes a support surface having a first part 22 and a pair of second parts 23 which extend in respective opposite directions from the first part. The first part 22 comprises a recess, the function of which will be explained subsequently.

The channel 14 also has a pair of side walls 24 sufficiently spaced apart for receiving the flexible tubing within the channel 14. Extending from side walls 24 are a pair of aligned retaining tabs 26 which terminate in ends which are spaced apart by a distance slightly less than the outer diameter of the flexible tubing. Retaining tabs 26 are also spaced from the arcuate bottom wall portion 16 so as to releasably retain and position the flexible tubing against the channel bottom wall and the anvil structure.

Figure 4:
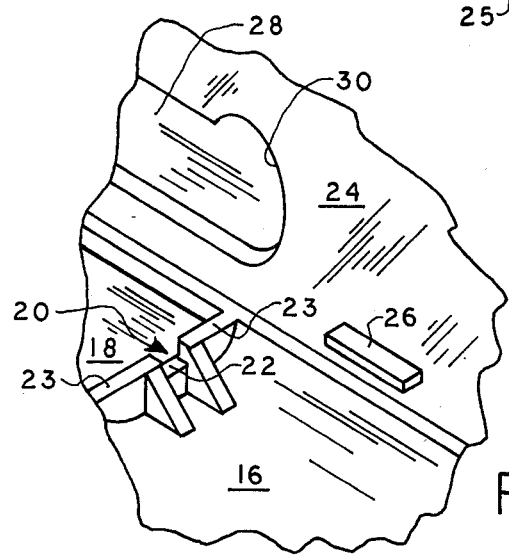
FIG. 4 is a partial, perspective view, to an enlarged scale illustrating particular inner channel structural details of the clamp of FIG. 1.
Figure 5:
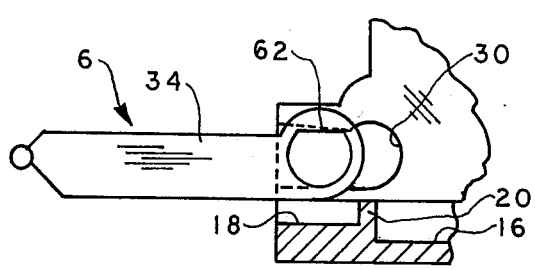
FIG. 5 is a partial side sectional view of the forward end of the clamp illustrating the cam and pivot arm prior to its retention in the clamp.

The channel side walls 24 in the forwardly extending portion 12 includes a pair of cylindrical slots 28 which terminate in arcuate end walls 30 as best seen in FIGS. 4 and 5. The effective diameter of the arcuate end walls is greater than the width dimension of the cylindrical slots 28.

Referring now to FIGS. 7 through 10, these Figures illustrate in detail the structure of the cam and pivot arm 6. The cam and pivot arm 6 includes a cam 32, a pivot arm 34, and a pair of trunnions 36 disposed on opposite sides of the cam 32. The cam 32 includes an arcuate or cylindrical cam surface 38 which forms an opposing structure to the support surface of the anvil structure 20 for confining the flexible tubing therebetween. The cam surface includes a first surface portion 40, a pair of peripheral surface portions 42, and a pair of intermediate surface portions 44 between the first surface portion 40 and the peripheral surface portions 42.

Figure 9:
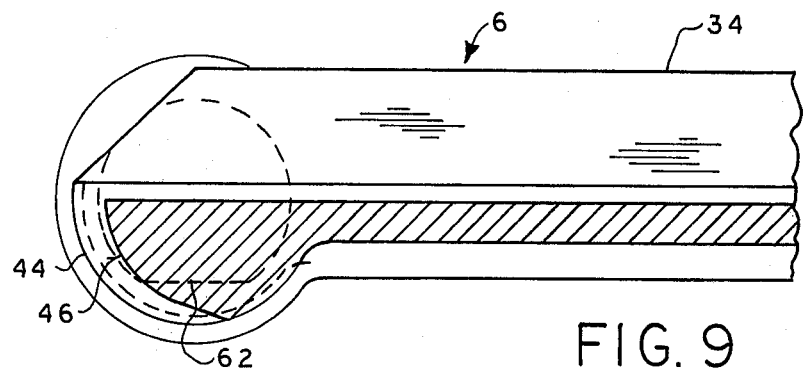
FIG. 9 is a cross-sectional view taken along lines 9—9 of FIG. 8.
Figure 10:
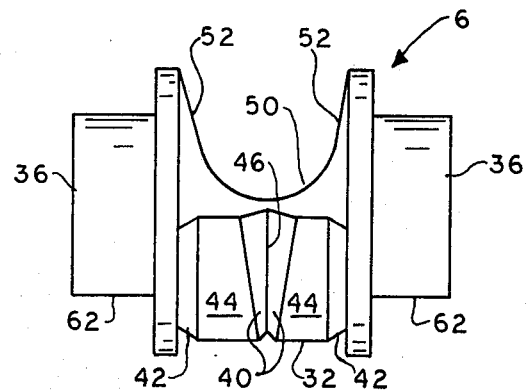
FIG. 10 is a view of the forward end of the cam and pivot arm.

The first surface portion 40 comprises a pair of converging side walls which result from the formation of a groove 46 within the cam 32. The groove 46 has a dimensioning depth with respect to the intermediate surface portion 44 as best seen in FIGS. 9 and 10.

The pivot arm 34 is integral to the cam 32 and extends from the cam and terminates in a handle 48. The pivot arm has a top wall 50 and a pair of side walls 52 which smoothly merge with the top wall 50 to form an arcuate channel dimensioned for receiving the flexible tubing.

Figure 6:
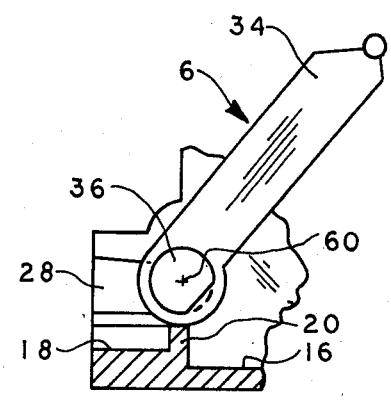
FIG. 6 is a partial sectional view similar to FIG. 5 but showing the cam and pivot arm after its retention in the clamp.

The trunnions 36 on opposite sides of the cam 32 coact with the arcuate end surfaces 30 of the slots 28 to allow the pivot arm and cam to pivot about an axis of rotation 60 as best seen in FIG. 6. The trunnions 36 include a substantially flat surface portion 62 defining a minimum dimension for the trunnions as opposed to the trunnion maximum dimension corresponding to the diameter dimensions of the trunnions. The minimum trunnion dimension allows the cam and pivot arm 6 to be slidingly received within the rectangular slots 28 of the forward portion 12 of housing 4. To that end, it is preferred that the width dimension of the rectangular slots 28 be substantially equal to the minimum dimension of the trunnions 36. As can be seen in FIG. 5, the substantially flat surface portion 62 of the trunnions are disposed substantially parallel to the upper walls of the slots 28 as the cam and pivot arm 26 is slid into the housing. The cam and pivot arm 6 is slid into the housing until the trunnions engage the arcuate end surfaces 38 of the slots. The effective diameter dimension of the arcuate curved end surfaces 30 of the slots is preferably equal to the diameter dimension of the trunnions. Hence, as shown in FIG. 6, as the pivot arm is rotated, it can be seen that the trunnions 36 will coact with the slots to lock the cam and pivot arm 6 within the clamp body. Additionally, it can be seen from FIG. 6, that when the cam and pivot arm 6 is so locked within the body, the surface of the cam will be closely adjacent the anvil structure 20 for controllably constricting a flexible tubing therebetween. Also, when the cam 32 is locked within the clamp body, the first surface portion of the cam is aligned with and closely adjacent to the recess first part 22 of the anvil structure 20 as shown in FIGS. 11 through 14.

Figure 11:
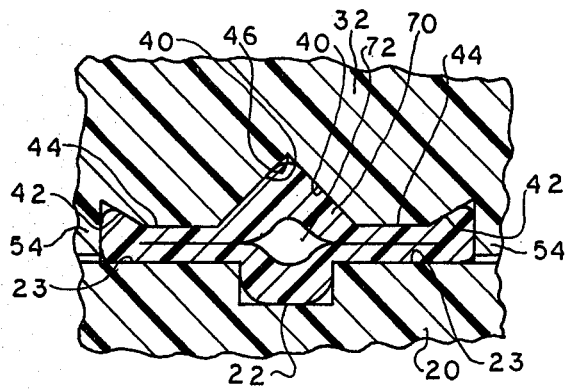
FIGS. 11 through 14 are partial, cross-sectional views, to an enlarged scale taken along a line through the supporting anvil and transverse to the flexible tubing illustrating the operation of the clamp for reducing the fluid flow passageway of the tubing progressively from an open position to a nearly closed position.
Figure 14:
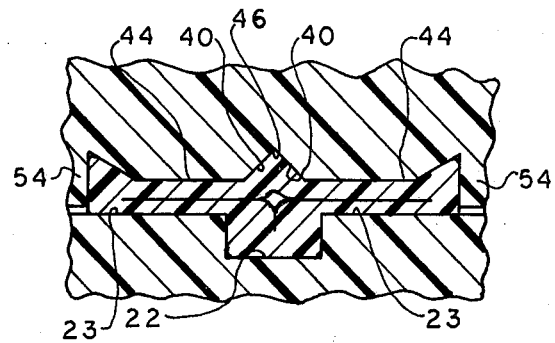
Figure 7:
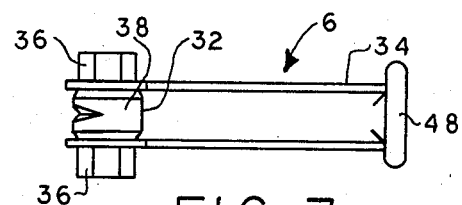
FIG. 7 is a top plan view of the cam and pivot arm.
Figure 8:
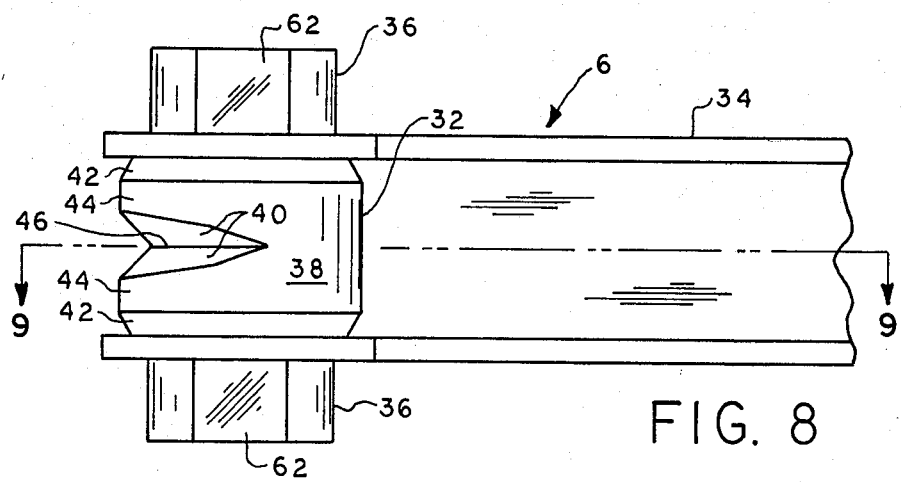
FIG. 8 is an enlarged, partial, top plan view of the cam and pivot arm.

Referring now to FIGS. 11 through 14, they illustrate the operation of the clamp for different pivotal positions of the cam from a substantially open position shown in FIG. 11 to a nearly closed position as shown in FIG. 14 for controlling the flow rate of fluid through the flexible tubing. The flexible tubing 70 is confined between the cam 32 and the anvil structure 20. The peripheral surface portions 42 are inclined relative to the intermediate surface portions 44 and coact with flanges 54 to constrict and shut off the tubing at peripheral spaced apart regions and to confine the tubing against lateral movement. The intermediate surface portions 44 coact with the anvil support surface second parts 23 to constrict opposed wall portions of the tubing by an amount sufficient to preclude fluid flow through the tubing in those areas where the anvil second parts and the intermediate surface portions are juxtaposed.

The first surface portion 40 coacts with the anvil support surface first part 22 for defining a space 72 for a reduced-flow passageway in the flexible tubing. It is in this passageway that the fluid flows.

Figure 12:
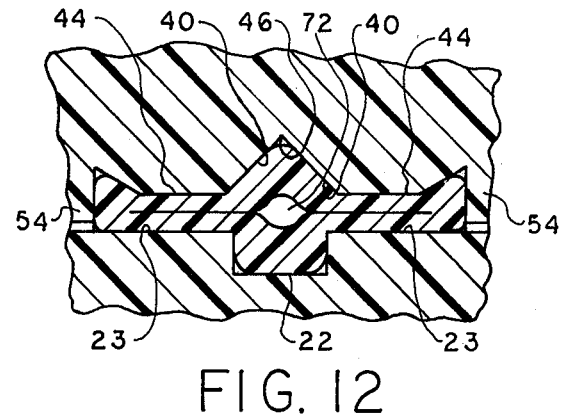
Figure 13:
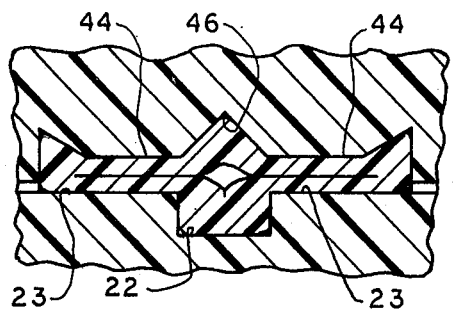

Preferably, each point along the intermediate surface portions 44 is equidistant from the axis of rotation 60 (FIG. 6) so that the distance between the intermediate surface portion 44 and the anvil second parts 23 is constant. However, because the groove 46 diminishes with respect to the intermediate surface portions 44, as the pivot arm is pivoted, the first surface portion 40 presents to the tubing and to the anvil first part 22 a plurality of similar triangles which are reduced in area as the pivot arm is pivoted from an open position shown in FIG. 11 to a nearly closed position as shown in FIG. 14. Each of these similar triangles has sides corresponding to first surface portion 40 and a base parallel to the anvil support surface and more specifically, the base of the similar triangles are along a line coincident with the intermediate surface portions 44. Hence, as seen in FIG. 12, the fluid flow passageway 72 has been reduced in size with pivotal movement of the cam because the point at which the side walls of the first surface portions 44 converge approaches the anvil structure. At the same time, the contact surface area of the intermediate surface portions with the tubing is increased. As a result, a maximum and constant constricting force is applied to the tubing by the intermediate surface portions 44 and the anvil second parts 23 to more accurately define the cross-sectional area of the fluid passageway 72 and to preclude inadvertent pulling of the flexible tubing longitudinally of the clamp during operation.

As can be seen from FIGS. 11 through 14, the series of similar triangles formed during the closing of the clamp comprise isosceles triangles and more particularly, isosceles right triangles having an apex angle at the groove or point of convergence 46 of the first surface portions 40 which is equal to 90°. The groove is preferably also positioned on the cam 32 so that metering of the fluid does not take place until the pivot arm has been pivoted through 90° of rotation. Once metering begins, a shield 21, which preferably constitutes an extension of one of the channel walls 24, prevents accidental movement of the pivot arm over the 90° of movement that are most critical and which will be generally used in intravenous feeding. Also, a pair of bifurcated projections 25 are provided to provide a temporary tube shut-off structure to be used when changing intravenous solution bottles without changing the flow rate.

Figure 15:
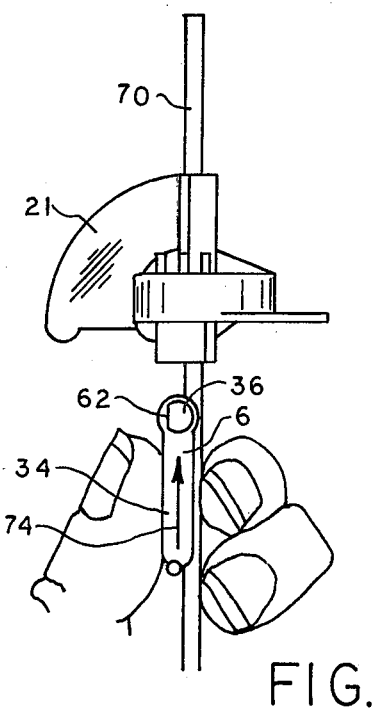
FIG. 15 is a side view illustrating the manner in which the clamp of the present invention may be mounted onto the flexible tubing of a sterile intravenous kit without disturbing the sterility of the kit.

Referring now to FIG. 15, it illustrates how the clamp of the present invention may be mounted to the flexible tubing 70 of a sterile intravenous set without disturbing the sterility of the intravenous set. The flexible tubing 70 is first placed into the channel 14 of the clamp body and pressed past the tabs 26 to lock releasably the flexible tubing against the bottom wall of the channel 14 and to position the flexible tubing 70 against the anvil support surface (FIG. 3). The cam and pivot arm 6 is then placed over the flexible tubing so that the channel of the pivot arm receives the flexible tubing. The pivot arm 34 is then slid into the body by inserting the trunnions 36 into the rectangular slots 28 with the substantially flat portions 62 of the trunnions being disposed parallel to the upper wall of the slots 28. The cam and pivot arm 6 is inserted in the direction of the arrow 74. Once the trunnions engage the arcuate end surfaces 30 of the slots, upon slight pivotal movement of the pivotal arm, the trunnions and arcuate end surfaces of the slots will coact to lock the pivot arm in place and position the cam in operative relation to the anvil structure. The pivot arm may then be further pivoted to adjust the clamp to provide the desired fluid flow rate through the flexible tubing.

Figure 16:
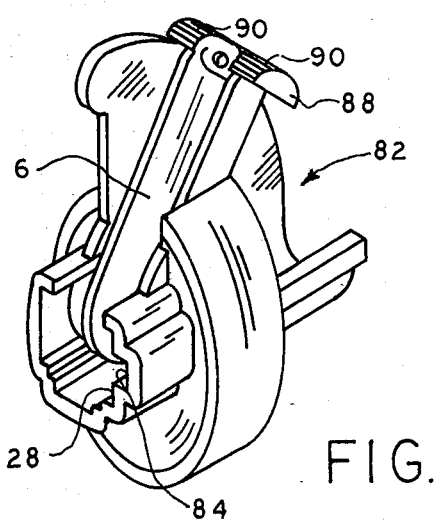
FIG. 16 is a perspective view of another clamp constructed in accordance with and embodying the present invention.
Figure 17:
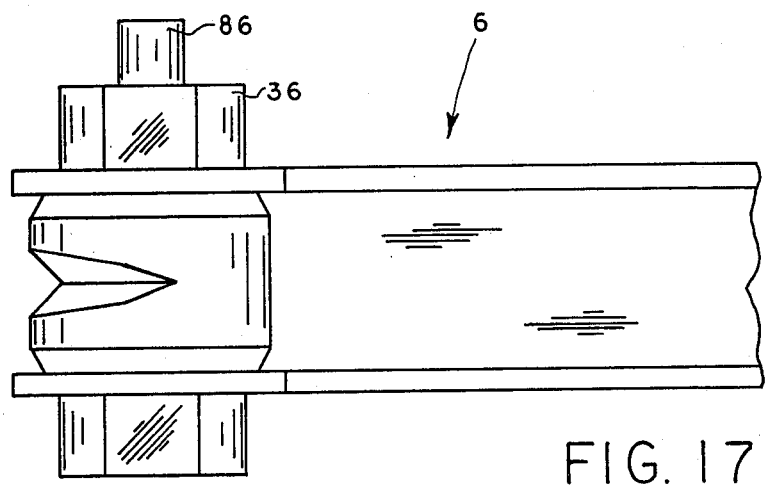
FIG. 17 is an enlarged, partial, top plan view of the cam and pivot arm of the clamp of FIG. 16.

Referring now to FIGS. 16 and 17, the clamp 82 thereshown is essentially identical to the clamp 2 of FIG. 1 except that the clamp 82 includes a key slot 84 in cylindrical slot 28, a key trunnion 86 extending from trunnion along a common axis, and an operating knob 88 having a knurled arcuate surface 90. In all other aspects, except for the absence of bifurcated projections 25 carried by the clamp 2 of FIG. 1, the operable structure of the clamp 82 is identical and therefore need not be described in detail.

The key slot 84 is dimension for receiving the key trunnion 86. As a result, the pivot arm 6 can be inserted into the clamp body in only one position assuring that the clamp 82 will be mounted to the tubing in the correct manner. This obviously is important because, when caring for a patient, the nurse or doctor has many other things in which to be concerned. This structure therefore provides complete assurance that the clamp will be applied to the tubing properly and function in the intended manner.

Figure 18:
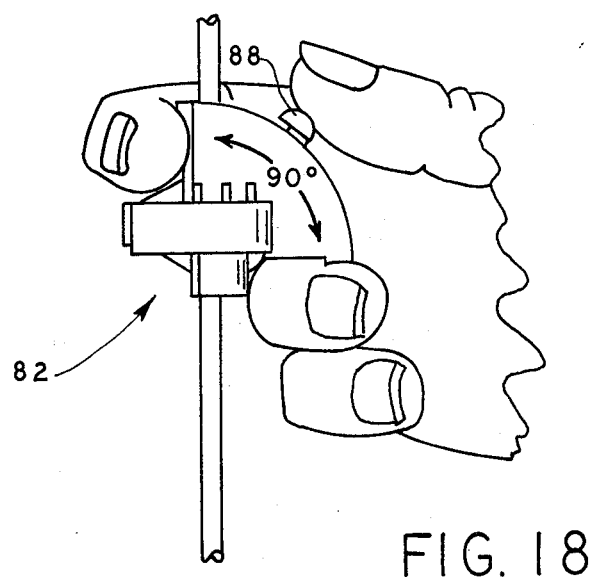
FIG. 18 is a side view, illustrating the manner in which the clamp of FIG. 16 may be operated with a single hand.

FIG. 18 shows how the knurled knot 88 of the pivot arm assists medical personnel in operating the clamp 82 with only one hand. The clamp is held as shown, with the thumb placed on the knurled knot 88 for adjusting the fluid flow rate through the tubing. As a result, the other hand is left free for assisting a patient with breathing, for example.

The invention is claimed as follows:

1. A clamp for providing a stable fluid flow rate through a flexible tubing, said clamp comprising a surface for supporting the tubing, said supporting surface including a first part and a pair of second parts extending in respective opposite directions from said first part, and tube constricting means forming an opposing structure to said support surface for confining the tube therebetween, said opposing structure including a first surface portion adjacent said supporting surface first part, a pair of peripheral surface portions, and a pair of intermediate surface portions between said first surface portion and said peripheral surface portions, said peripheral surface portions coacting with said supporting surface second parts for compressing diametrically opposed wall portions of the tubing an amount sufficient to shut off the tubing at peripheral spaced apart regions, said first surface portion coacting with said support surface first part for defining a space for a reduced-flow passageway in the tubing, and said intermediate surface portions coacting with said support surface second parts for constricting the tubing therebetween, said constricting means including an arm structure pivotal about a fixed axis relative to said support surface for gradually increasing the constricting contact surface area of said intermediate surface portions with the tubing along a line parallel to said support surface second parts and for gradually reducing the transverse dimension of said first surface portion and said space for reduced-flow passageway in the tubing as said constricting means is pivoted from an open position to a closed position and wherein said first surface portion comprises a pair of walls converging in a direction away from said support surface wherein the point at which said walls converge approaches the plane of said intermediate surface portions as said constricting means is pivoted from said open position to said closed position.

2. A clamp as defined in claim 1 wherein the spacing between said intermediate surface portions and said support surface parts is constant for each pivotal position of said constricting means between said open position and said closed position.

3. A clamp as defined in claim 1 wherein said converging walls and said plane of said intermediate surface portions define a plurality of similar triangles which decrease in size as said point of convergence of said walls approaches said plane of said intermediate surface portions and as said constricting contact surface area of said intermediate surface portion simultaneously increases upon said constricting means being pivoted from said open position to said closed position, each of said plurality of triangles having a base which coincides with said plane of said intermediate surface portions.

4. A clamp as defined in claim 3 wherein said similar triangles are isosceles triangles.

5. A clamp as defined in claim 4 wherein the apex angle of said isosceles triangles is approximately 90°.

6. A clamp according to claim 1 including means for receiving and retaining said tubing assembled with the clamp prior to assembly of said constricting means with the remainder of the clamp.

7. A clamp for providing a stable fluid flow rate through a flexible tubing, said clamp comprising a support surface for supporting the tubing, said support surface including a first part and a pair of second parts extending in respective opposite directions from said first part, and tube constricting means comprising a cam rotatable about an axis of rotation and having an arcuate surface forming an opposing structure to said support surface for confining the tube therebetween, said cam including a peripheral groove adjacent said first part having a pair of side walls converging in a direction toward said axis of rotation and having a depth which diminishes over an arcuate portion of said cam, said arcuate surface also including a peripheral surface portion at each end of said cam and intermediate surface portions between said groove and said peripheral surface portions, said peripheral surface portions coacting with said support surface second parts for compressing diametrically opposed wall portions of the tubing an amount sufficient to shut off the tubing at peripheral spaced apart regions, said cam groove and said support surface first part coacting to provide a space for a reduced-flow passageway in the tubing, and said intermediate surface portions coacting with said support surface second parts for constricting the tubing therebetween, said cam being rotatable from an open position whereat said groove has its maximum depth adjacent to said support surface first part to a closed position whereat said groove has its minimum depth adjacent to said support surface first part for gradually increasing the constricting contact surface area of said intermediate surface portions with the tubing along a plane parallel to and constantly spaced from said support surface and for simultaneously reducing the dimension of said groove acting upon the tubing with said support surface first part for reducing said flow passageway in the tubing.

8. A clamp as defined in claim 7 wherein said converging side walls of said groove and said plane of said intermediate surface portion define a plurality of similar triangles which decrease in size relative to the support surface as said cam is rotated from said open position to said closed position.

9. A clamp as defined in claim 8 wherein said similar triangles are isosceles triangles.

10. A clamp as defined in claim 9 wherein the apex angle of said isosceles triangles is approximately 90°.

11. A clamp as defined in claim 7 wherein said support surface comprises an anvil and wherein said support surface first part comprises a recess in said anvil.

12. A clamp as defined in claim 7 wherein said cam further includes a cylindrical flange at each end thereof for confining the tubing against lateral movement in said peripheral spaced apart regions.

13. A clamp for providing a stable fluid flow rate through a flexible tubing which is adapted to be readily mounted onto the tubing comprising a body having a channel dimensioned to receive the tubing, said channel having a pair of sidewalls and a bottom wall including an anvil for supporting the tubing, and constricting means providing an opposed structure to said anvil and coacting with said anvil for controllably compressing the tubing to establish a stable fluid flow rate through the tubing, said channel having an opening along its entire length for receiving the tubing therein against said bottom wall, means for receiving and retaining said constricting means in an operating position spaced from and adjacent to said anvil, and wherein said constricting means comprises a rotatable cam having a pivot arm extending therefrom and a trunnion adjacent opposite sides of said cam, said trunnions being generally cylindrical in shape and having a flat peripheral surface portion defining a minimum trunnion dimension which is less than the trunnion diameter dimension and wherein said channel constricting means receiving and retaining means includes a slot extending along each said sidewall, each said slot including an initial dimension substantially equal to said trunnion minimum dimension and an arcuate end wall having an effective diameter dimension substantially equal to said trunnion diameter dimension, said slots being adapted to slidingly receive said trunnions and to retain said trunnions upon rotation of said pivot arm.

14. A clamp as defined in claim 13 wherein said lever arm includes a tubing receiving channel having a pair of sidewalls and a topwall and wherein said trunnion flat surface portions are substantially parallel to said pivot arm channel top wall for enabling said lever arm to be placed over said tube and to be slid into said slots.

15. A clamp for providing a stable fluid flow rate through a flexible tubing which is adapted to be readily mounted onto the flexible tubing comprising a body having a channel dimensioned to receive the tubing, said channel having a pair of sidewalls and a bottom wall including an anvil for supporting the tubing, constricting means comprising a cam rotatable about an axis of rotation and a pivot arm, said cam having a cam surface including means for coacting with said anvil to define a space for a reduced-flow passageway in the tubing and for varying the dimensions of said space as said cam is rotated to adjust the fluid flow rate through the tubing, said cam also including a trunnion at each end thereof, said trunnions having a generally cylindrical surface portion defining a predetermined diameter dimension and a flat surface portion defining a minimum dimension, and a slot in each said channel side wall, each said slot having an initial portion dimensioned substantially equal to said minimum trunnion dimension and an end portion having an arcuate surface portion having an effective diameter substantially equal to said trunnion predetermined diameter for initially receiving said cam and pivot arm with said trunnion flat surfaces against a top wall of said slot end portion and locking said trunnion therein in response to slight pivoting of said pivot arm, said slot end portions being adjacent said anvil for positioning said cam in operative relation to said anvil.

16. A clamp as defined in claim 15 wherein said pivot arm includes a second channel for receiving the tubing for enabling said cam to be assembled to said body within said slots after the tubing has been received in said body and supported on said anvil.

17. A clamp as defined in claim 15 wherein one said channel side wall further includes a key slot, wherein said cam includes a key trunnion extending from one of said trunnions, and said key slot being dimensioned for receiving said key trunnion for enabling said cam to be received by said body in only one position.

18. A clamp as defined in claim 15 wherein said pivot arm includes a knurled knob at one end thereof.

* * * * *

UNITED STATES PATENT AND TRADEMARK OFFICE
CERTIFICATE OF CORRECTION

PATENT NO. : 4,272,051
DATED : June 9, 1981
INVENTOR(S) : JAMES A. HUGGINS

It is certified that error appears in the above-identified patent and that said Letters Patent are hereby corrected as shown below:

Column 4, line 13, change "portion 8" to --portion 18--;

Column 5, line 9, change "pivot arm 26" to --pivot arm 6--;

Column 6, line 59, change "dimension" to --dimensioned--;

Column 7, line 1, change "knot" to --knob--;

Column 7, line 4, change "knot" to --knob--;

Column 7, line 47, after "surface" insert --second--.

Signed and Sealed this

Fifteenth Day of September 1981

[SEAL]

Attest:

GERALD J. MOSSINGHOFF

Attesting Officer

Commissioner of Patents and Trademarks